US009023058B2

(12) United States Patent
Jaramillo et al.

(10) Patent No.: US 9,023,058 B2
(45) Date of Patent: May 5, 2015

(54) SURGICAL INSTRUMENT AND METHOD FOR TENSIONING AND SECURING A FLEXIBLE SUTURE

(75) Inventors: Jorge Jaramillo, Burnaby (CA); Doug Goertzen, New Westminster (CA); Kevin Chaplin, Vancouver (CA); Daniel Gelbart, Vancouver (CA)

(73) Assignee: Kardium Inc., Burnaby, BC (CA)

( * ) Notice: Subject to any disclaimer, the term of this patent is extended or adjusted under 35 U.S.C. 154(b) by 466 days.

(21) Appl. No.: 12/246,614

(22) Filed: Oct. 7, 2008

(65) Prior Publication Data
US 2010/0087836 A1 Apr. 8, 2010

(51) Int. Cl.
*A61B 17/10* (2006.01)
*A61B 17/88* (2006.01)
*A61B 17/04* (2006.01)
*A61B 17/82* (2006.01)
*A61B 19/00* (2006.01)

(52) U.S. Cl.
CPC .............. *A61B 17/8869* (2013.01); *A61B 17/04* (2013.01); *A61B 17/0467* (2013.01); *A61B 17/823* (2013.01); *A61B 17/8861* (2013.01); *A61B 2017/0496* (2013.01); *A61B 2019/464* (2013.01); *A61B 2019/4836* (2013.01)
USPC ............ 606/103; 606/139; 606/144; 606/148

(58) Field of Classification Search
USPC .................. 606/74, 103, 139, 144–146, 148; 623/13.13
See application file for complete search history.

(56) References Cited

U.S. PATENT DOCUMENTS

| 2,943,650 | A | 7/1956 | Rubin | |
|---|---|---|---|---|
| 3,959,960 | A | 6/1976 | Santos | |
| 4,527,554 | A | 7/1985 | Klein | |
| 5,021,059 | A | 6/1991 | Kensey et al. | 606/213 |
| 5,100,418 | A | 3/1992 | Yoon et al. | 606/139 |
| 5,156,609 | A | 10/1992 | Nakao et al. | 606/142 |
| 5,320,632 | A | 6/1994 | Heidmueller | 606/144 |

(Continued)

FOREIGN PATENT DOCUMENTS

WO 2007/115390 10/2007
WO 2008/073947 A2 6/2008

OTHER PUBLICATIONS

Lichtenstein et al., "System for Improving Diastolic Dysfunction," U.S. Appl. No. 11/497,309, filed Aug. 2, 2006, 13 pages.

(Continued)

*Primary Examiner* — Jerry Cumberledge
*Assistant Examiner* — Nicholas Plionis
(74) *Attorney, Agent, or Firm* — Rossi, Kimms & McDowell LLP

(57) ABSTRACT

A surgical instrument may be used to apply tension to a flexible suture to close and secure a broken or cut bone (e.g. a sternum following a sternotomy). The device preferably applies an adjustable tension to the flexible suture in order to secure the bone together. Multiple instruments may be used together to ensure the desired tension is applied to the entire bone structure being secured with the flexible sutures. Once the desired tension is achieved, the device preferably provides a mechanism to apply a uniform twist to the flexible suture to lock the flexible suture in place and maintain the tension previously achieved. The device may automatically cut the flexible suture, or the flexible suture may be cut by the surgeon once the twisting action has been performed.

45 Claims, 17 Drawing Sheets

(56) References Cited

U.S. PATENT DOCUMENTS

| | | | | |
|---|---|---|---|---|
| 5,364,408 | A | 11/1994 | Gordon | 606/144 |
| 5,366,459 | A | 11/1994 | Yoon | 606/151 |
| 5,368,601 | A | 11/1994 | Sauer et al. | 606/144 |
| 5,374,275 | A | 12/1994 | Bradley et al. | 606/144 |
| 5,417,698 | A | 5/1995 | Green et al. | |
| 5,478,353 | A | 12/1995 | Yoon | 606/213 |
| 5,690,649 | A * | 11/1997 | Li | 606/139 |
| 5,728,114 | A | 3/1998 | Evans et al. | 606/148 |
| 5,782,861 | A | 7/1998 | Cragg et al. | 606/216 |
| 5,865,791 | A | 2/1999 | Whayne et al. | 604/49 |
| 5,919,207 | A | 7/1999 | Taheri | 606/219 |
| 5,961,440 | A | 10/1999 | Schweich, Jr. et al. | 600/16 |
| 5,971,994 | A | 10/1999 | Fritzsch | |
| 5,980,473 | A | 11/1999 | Korakianitis et al. | |
| 5,984,950 | A | 11/1999 | Cragg et al. | 606/216 |
| 6,113,610 | A | 9/2000 | Poncet | 606/139 |
| 6,241,747 | B1 | 6/2001 | Ruff | 606/216 |
| 6,248,124 | B1 | 6/2001 | Pedros et al. | 606/213 |
| 6,258,258 | B1 | 7/2001 | Sartori et al. | |
| 6,358,258 | B1 | 3/2002 | Arcia et al. | 606/139 |
| 6,391,048 | B1 | 5/2002 | Ginn et al. | 606/213 |
| 6,432,115 | B1 * | 8/2002 | Mollenauer et al. | 606/148 |
| 6,506,210 | B1 | 1/2003 | Kanner | 606/213 |
| 6,575,971 | B2 | 6/2003 | Hauck et al. | 606/52 |
| 6,626,930 | B1 | 9/2003 | Allen et al. | 606/213 |
| 6,676,685 | B2 | 1/2004 | Pedros et al. | 606/213 |
| 6,743,241 | B2 | 6/2004 | Kerr | 606/144 |
| 6,752,810 | B1 * | 6/2004 | Gao et al. | 606/103 |
| 6,960,229 | B2 | 11/2005 | Mathis et al. | 623/2.36 |
| 6,986,775 | B2 | 1/2006 | Morales et al. | 606/139 |
| 7,674,276 | B2 | 3/2010 | Stone et al. | |
| 2001/0003158 | A1 | 6/2001 | Kensey et al. | 606/213 |
| 2001/0005787 | A1 | 6/2001 | Oz et al. | 606/142 |
| 2003/0028202 | A1 | 2/2003 | Sancoff et al. | 606/144 |
| 2003/0208210 | A1 | 11/2003 | Dreyfuss et al. | 606/144 |
| 2004/0193187 | A1 * | 9/2004 | Boehringer et al. | 606/144 |
| 2005/0055089 | A1 | 3/2005 | Macoviak et al. | 623/2.37 |
| 2005/0090840 | A1 | 4/2005 | Gerbino et al. | 606/148 |
| 2005/0107871 | A1 | 5/2005 | Realyvasquez et al. | 623/2.11 |
| 2005/0125030 | A1 | 6/2005 | Forsberg et al. | 606/213 |
| 2005/0131441 | A1 | 6/2005 | Iio et al. | |
| 2005/0149014 | A1 | 7/2005 | Hauck et al. | 606/41 |
| 2005/0197694 | A1 | 9/2005 | Pai et al. | 623/2.1 |
| 2006/0015038 | A1 | 1/2006 | Weymarn-Scharli | 600/585 |
| 2006/0135968 | A1 | 6/2006 | Schaller | 606/144 |
| 2006/0135970 | A1 | 6/2006 | Schaller | 606/152 |
| 2006/0184242 | A1 | 8/2006 | Lichtenstein | 623/2.37 |
| 2007/0089617 | A1 | 4/2007 | Legtenberg et al. | |
| 2007/0198058 | A1 | 8/2007 | Gelbart et al. | 606/213 |
| 2007/0213578 | A1 | 9/2007 | Khairkhahan et al. | 600/16 |
| 2007/0225736 | A1 | 9/2007 | Zeiner et al. | 606/148 |
| 2008/0045778 | A1 | 2/2008 | Lichtenstein et al. | 600/16 |
| 2008/0269785 | A1 | 10/2008 | Lampropoulos et al. | 606/144 |
| 2008/0275477 | A1 | 11/2008 | Sterrett et al. | 606/148 |
| 2009/0287304 | A1 | 11/2009 | Dahlgren et al. | 623/2.37 |
| 2010/0087837 | A1 | 4/2010 | Jaramillo et al. | |
| 2011/0087227 | A1 | 4/2011 | Mazur et al. | |

OTHER PUBLICATIONS

International Search Report, mailed Sep. 10, 2010, for PCT/US2010/021835, 4 pages.

Written Opinion, mailed Sep. 10, 2010, for PCT/US2010/021835, 6 pages.

Extended European Search Report, dated Sep. 26, 2013, for Application No. 10772405.6, 6 pages.

Jaramillo et al., "Surgical Instrument and Method for Tensioning and Securing a Flexible Structure," Office Action mailed Jul. 8, 2011 for U.S. Appl. No. 12/436,926, 13 pages.

Jaramillo et al., "Surgical Instrument and Method for Tensioning and Securing a Flexible Structure," Amendment filed Oct. 5, 2011 for U.S. Appl. No. 12/436,926, 32 pages.

Jaramillo et al., "Surgical Instrument and Method for Tensioning and Securing a Flexible Structure," Office Action mailed Jan. 11, 2012 for U.S. Appl. No. 12/436,926, 21 pages.

Jaramillo et al., "Surgical Instrument and Method for Tensioning and Securing a Flexible Structure," Amendment filed Feb. 27, 2012 for U.S. Appl. No. 12/436,926, 25 pages.

Jaramillo et al., "Surgical Instrument and Method for Tensioning and Securing a Flexible Structure," Amendment filed Dec. 4, 2012 for U.S. Appl. No. 12/436,926, 19 pages.

Jaramillo et al., "Surgical Instrument and Method for Tensioning and Securing a Flexible Suture", Office Action mailed Sep. 21, 2012 for U.S. Appl. No. 12/436,926, 14 pgs.

Jaramillo et al., "Surgical Instrument and Method for Tensioning and Securing a Flexible Suture", Office Action mailed Sep. 20, 2013 for U.S. Appl. No. 12/436,926, 14 pgs.

Jaramillo et al., "Surgical Instrument and Method for Tensioning and Securing a Flexible Suture", Amendment filed Dec. 20, 2013 for U.S. Appl. No. 12/436,926, 21 pgs.

Jaramillo et al., "Surgical Instrument and Method for Tensioning and Securing a Flexible Suture", Office Action mailed Apr. 24, 2014 for U.S. Appl. No. 12/436,926, 17 pgs.

Jaramillo et al., "Surgical Instrument and Method for Tensioning and Securing a Flexible Suture", Amendment filed Jun. 16, 2014 for U.S. Appl. No. 12/436,926, 17 pgs.

Jaramillo et al., "Surgical Instrument and Method for Tensioning and Securing a Flexible Suture", Notice of Allowance mailed Jul. 14, 2014 for U.S. Appl. No. 12/436,926, 5 pgs.

Jaramillo et al., "Surgical Instrument and Method for Tensioning and Securing a Flexible Suture", 312 Amendment filed Sep. 3, 2014 for U.S. Appl. No. 12/436,926, 3 pgs.

European Examination Report issued in counterpart application No. EP10772405.6, dated Feb. 17, 2015.

* cited by examiner

SURGICAL INSTRUMENT AND METHOD FOR TENSIONING AND SECURING A FLEXIBLE SUTURE

BACKGROUND

1. Field

This disclosure is generally related to securing bones using a flexible suture and more particularly to surgical instruments suitable for securing the sternum with flexible sutures following a sternotomy

2. Description of the Related Art

During an open heart procedure, the patient's sternum is cut in half lengthwise in a procedure called a median sternotomy. At the end of the surgery, the two halves are brought together and secured with standard surgical wire sutures. The wire sutures may be placed around or through the sternum, and tension may be applied to the wire sutures to bring the two separated parts of the sternum together. Once in place, with the desired tension, the wire suture is then twisted together on itself in a helical pattern to lock the wire suture in place and prevent separation, or dehiscence of the sternum. This is typically done using surgical pliers to tension and twist the wire sutures together, but other methods may be used.

Dehiscence of the sternum is a serious concern for patients, hospitals and surgeons, occurring in an estimated 2.5% of all sternotomies. The dehiscence delays healing, may be uncomfortable for the patient, and increases the likelihood of infection which typically requires additional surgery to treat.

While securing the sternum together with the wire sutures, the surgeon attempts to apply sufficient tension so that the sternum is held together and does not dehisce following surgery. The surgeon also attempts to twist the wire sutures uniformly so that the wire sutures do not become unlocked and loosen following surgery, which may allow the sternum to dehisce. The surgeon would also like to ensure that the wire sutures do not break while being tensioned and twisted. Should a wire suture break, it may require the surgeon to replace all the wire sutures that have previously been tensioned and twisted, and the sternum closure be started again.

Instruments and methods for attaching a wire suture to two parts of a bone to hold the bone together and apply a tension to the wire suture are well known in the prior art. Various methods for locking the tensioned wire suture are also described in the prior art, including ferrules, crimps or twisting. Various methods of threading the wire suture through, or around the sternum have also been described in the literature, and methods such as single loops, double loops, or figure of eight loops may be used by surgeons to secure the sternum.

BRIEF SUMMARY OF THE INVENTION

Various embodiments of surgical instruments and methods for providing a desired tension to a flexible suture, and providing a twist to said flexible suture while under the desired tension, are described herein. One example of a flexible suture is a stainless steel wire suture as used in a sternal closure after a median sternotomy.

At least one embodiment of a surgical instrument may be summarized as comprising a mechanism for tensioning a flexible suture encircling a bone, a second mechanism for applying a plurality of twists to a flexible suture used to secure a flexible suture to a bone while maintaining tension in said suture, and a base that supports the surgical instrument on a bone during tensioning of a flexible suture. They flexible suture may be a stainless steel wire suture.

The surgical instrument may further include a base that comprises an open slot and at least one moveable member to constrain a flexible suture in the slot. The base preferably does not rotate relative to the bone. The surgical instrument may additionally comprise a slot to allow cutting of a flexible suture by a tool or comprise a mechanism for cutting a flexible suture. The surgical instrument may restrict a second flexible suture from being tensioned with the same surgical instrument. The surgical instrument may remain in a locked position after tensioning a flexible suture and restrict a second flexible suture from being tensioned with the same surgical instrument. The surgical instrument may be attached to a flexible suture before the suture is moved proximate to or encircles the bone. The surgical instrument preferably tensions the flexible suture before securing the suture by twisting.

At least one embodiment of a surgical instrument may be summarized as comprising a mechanism for tensioning a flexible suture encircling a bone, a second mechanism for applying a plurality of twists to a flexible suture used to secure a flexible suture to a bone while maintaining tension in said suture, and a removable handle used to drive at least one of the mechanisms. The flexible suture may be a stainless steel wire suture.

The surgical instrument may further include a mechanism for tensioning which comprises a one way clutch that restricts the release of tension from a flexible suture after tension has been applied to the flexible suture The surgical instrument may further include a mechanism for tensioning comprising one or more springs which are compressed as a flexible suture is tensioned. The instrument may further provide an indication of the tension applied to said flexible suture. The surgical instrument may restrict a second flexible suture from being tensioned with the same surgical instrument. The surgical instrument may remain in a locked position after tensioning a first flexible suture and restrict a second flexible suture from being tensioned with the same tool.

At least one embodiment of a surgical instrument may be summarized as comprising a mechanism for tensioning a flexible suture encircling a bone where the mechanism for tensioning comprises at least one member for securing at least one end of a flexible suture, a second mechanism for applying a plurality of twists to a flexible suture, and an open slot extending from the base of the surgical instrument to the member for securing at least one flexible suture, in which at least one end of said flexible suture is carried. The flexible suture may be a stainless steel wire suture.

The surgical instrument may further include a mechanism for tensioning that comprises a one way clutch that restricts the mechanism from returning to the initial configuration of the mechanism after the surgical instrument is released from a flexible suture encircling a bone.

The surgical instrument may further include a mechanism for applying a plurality of twists that comprises at least two members which are drawn together as tension is applied to a flexible suture and rotate inside a shaft as said plurality of twists are applied. The instrument may also provide an indication of the tension applied to a flexible suture.

The surgical instrument may further include a member for securing at least one end of a flexible suture that is a hole in a rotating shaft. The surgical instrument may restrict a second flexible suture from being tensioned with the same surgical instrument. The surgical instrument may remain in a locked position after tensioning a flexible suture and restrict a second flexible suture from being tensioned with the same surgical instrument.

At lease one embodiment of a surgical instrument may be a single-use instrument for securing parts of a bone using a flexible suture, comprising a mechanism for fixing at least one of said sutures to said instrument prior to said suture encircling said bone, and a second mechanism for tensioning said suture prior to securing said suture by twisting.

Yet another embodiment is a system for securing parts of a bone using flexible sutures comprising a plurality of single-use surgical instruments, each said instrument comprising a mechanism for fixing at least one end of a flexible suture to said instrument prior to said suture encircling said bone.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE INVENTION

In the following description, certain specific details are set forth in order to provide a thorough understanding of various embodiments of the invention. However, one skilled in the art will understand that the invention may be practiced without these details. In other instances, well-known structures have not been shown or described in detail to avoid unnecessarily obscuring descriptions of the embodiments of the invention.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings provided herein are for convenience only and do not interpret the scope or meaning of the claimed invention.

References in the document are made to a stainless steel wire sutures, which could also refer to any other type of flexible suture.

Figure 1:
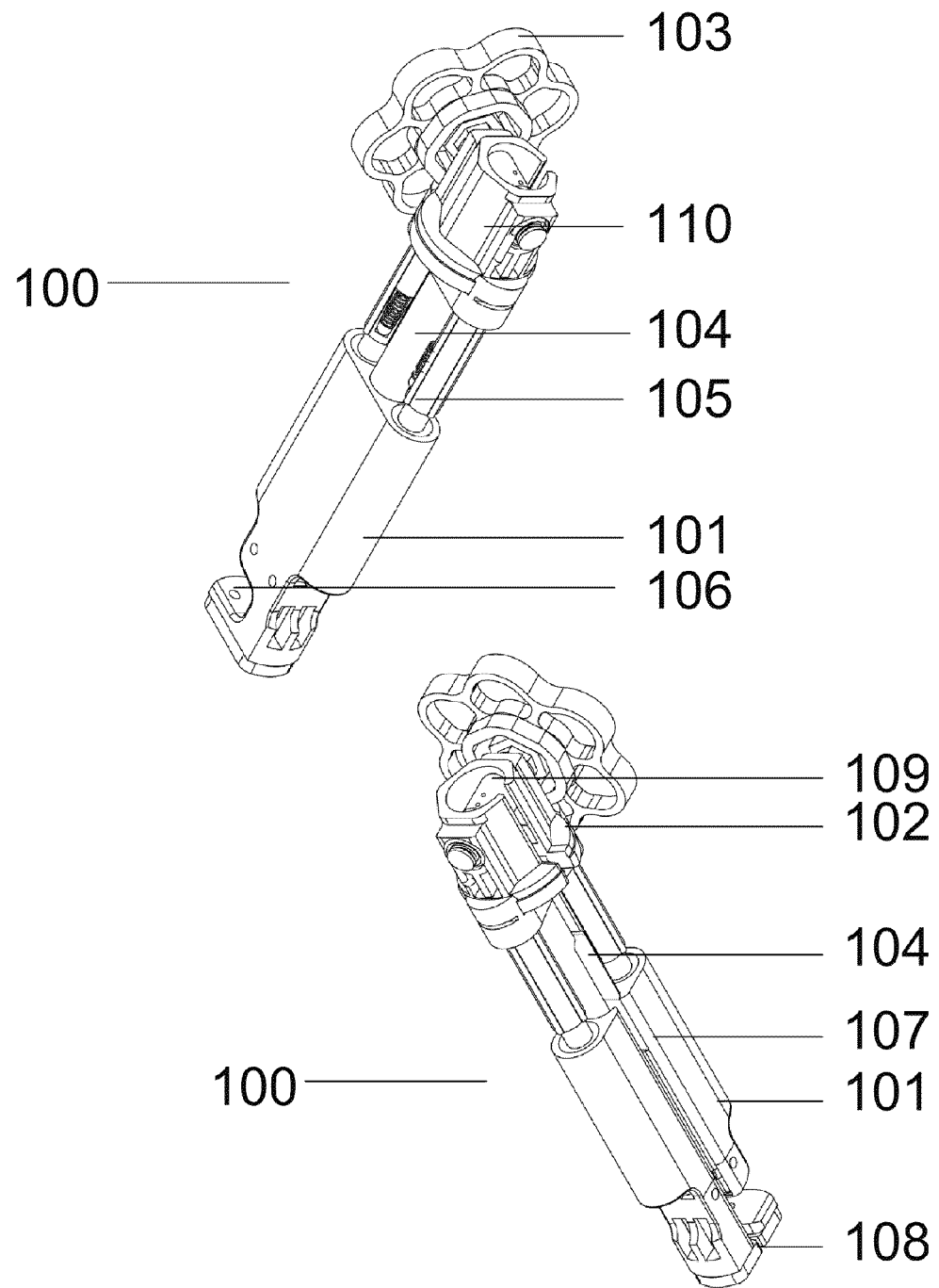
FIG. 1 is a schematic diagram showing two views of a surgical instrument according to one illustrated embodiment.

FIG. 1 shows an assembled view of a surgical instrument according to one illustrated embodiment. Surgical instrument 100 comprises base column 101, rotating head 102, tensioning handle 103, central twisting shaft 104 and pistons 105. Surgical instrument 100 may also have cutting slot 106. Surgical instrument 100 comprises open slot 107 that runs vertically through surgical instrument 100. Surgical instrument 100 is so designed, such that a flexible suture or multiple flexible sutures may be loaded into slot 107 and easily drawn into the centre of surgical instrument 100 without being threaded or fed through a lumen or hole. Slot 107 preferably runs through base 108, base column 101, rotating head 102 and central twisting shaft 104. A flexible suture may be secured into tensioning shaft 109 prior to being drawn into open slot 107, or after the flexible suture has been drawn into open slot 107. The surgical instrument may be manufactured in such a way and of such materials that it is to be disposed of after a single use. A single-use instrument may be used to perform a particular action once, or to perform a set of actions, but only on a single patient. An example of performing a particular action once is tensioning and twisting a single flexible suture used to secure a portion of the sternum after a sternotomy. An example of performing a set of actions on a single patient is tensioning and twisting all, or at least more than one of, the flexible sutures used to secure the sternum after a sternotomy. There are several reasons why it may be preferable for a particular surgical instrument to be "single use" including the ability to ensure proper sterilization and the ability to produce a more cost-effective product. Several examples of apparatus that may restrict the number of actions a particular surgical instrument may perform include a mechanism that locks the device in a position after the first use such that it cannot be used again, components fabricated out of a material such as plastic that becomes deformed after one or several uses and causes the device to fail, or parts that cannot be sterilized after use.

Figure 2:
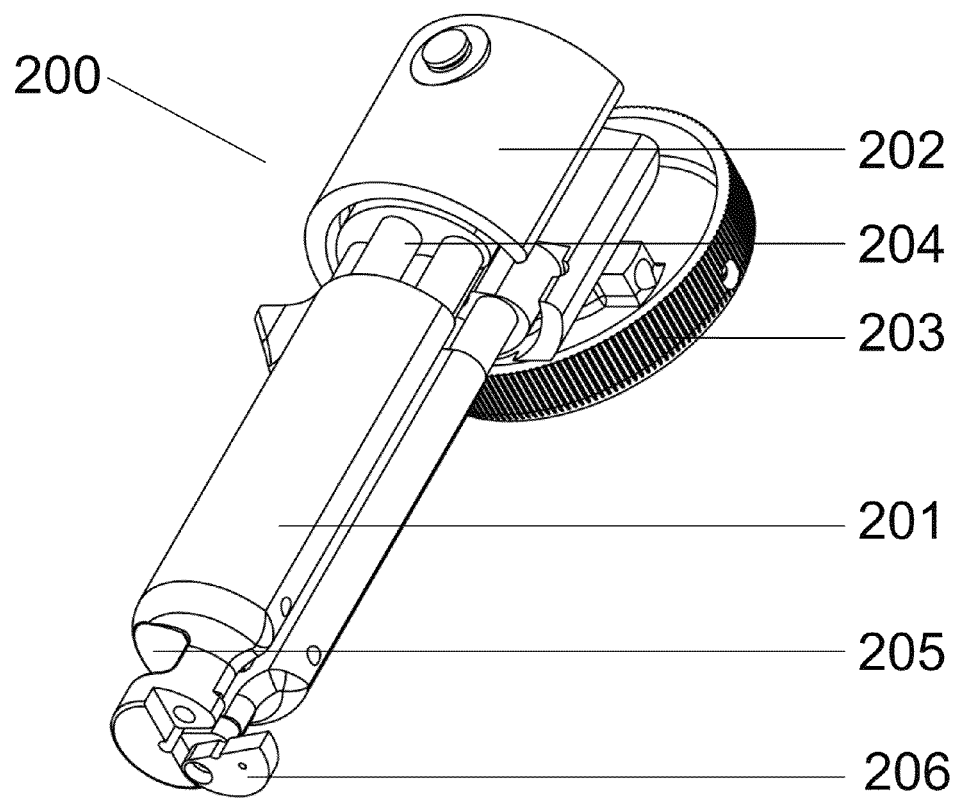
FIG. 2 is a schematic diagram of a surgical instrument according to another illustrated embodiment.

FIG. 2 shows an assembled view of a surgical instrument according to another illustrated embodiment. Surgical instrument 200 comprises base column 201, rotating head 202, and tensioning handle 203. Also shown are pistons 204 and cutting slot 205. Flexible suture capture lock 206 is also shown.

Figure 3:
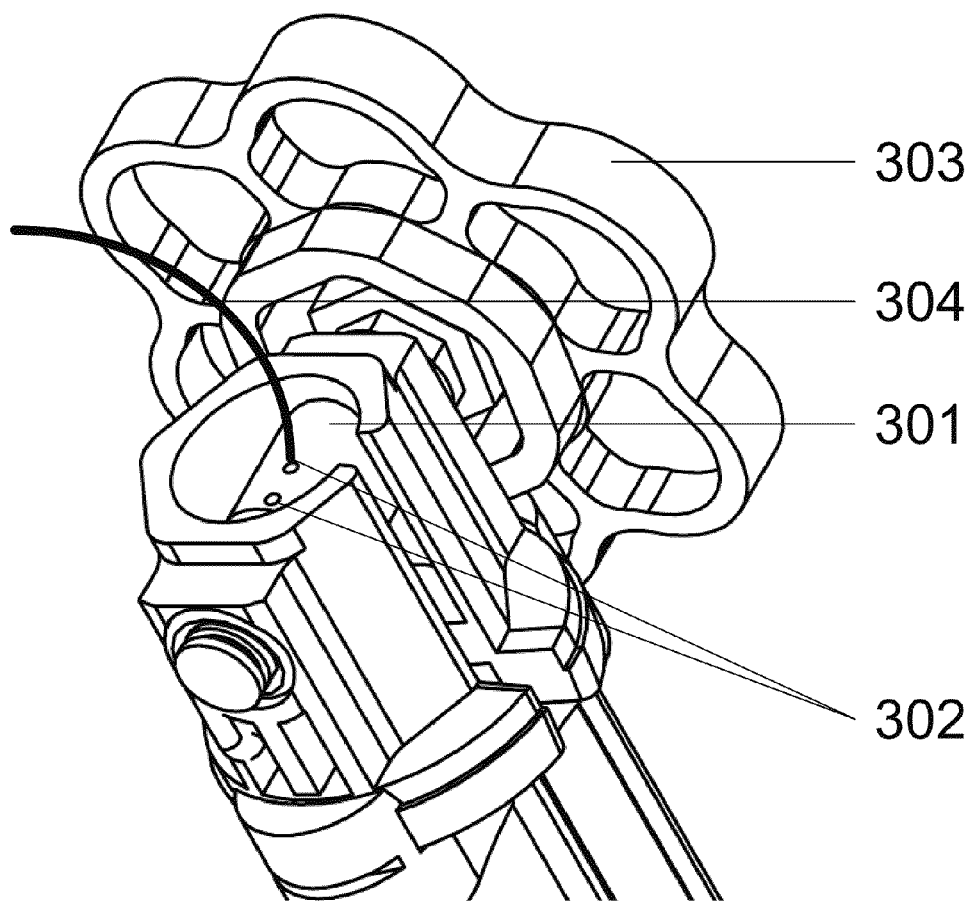
FIG. 3 is a diagram showing a detailed view of a head assembly of a surgical instrument, according to one illustrated embodiment.

FIG. 3 shows one embodiment of how flexible suture 304 may be secured in tensioning shaft 301. One or more small holes 302 may be made in tensioning shaft 301. The ends of flexible suture 304 may be inserted into holes 302. Rotating tensioning shaft 301 by rotating tensioning handle 303 causes flexible suture 304 to wrap around tensioning shaft 301, and so become secured to tensioning shaft 301. In other embodiments there may be multiple holes 302 at various angles that allow flexible suture 304 to be easily inserted, regardless of the orientation of tensioning shaft 301. Flexible suture 304 may be inserted into small holes 302 either horizontally, from below, or from above. Flexible suture 304 may be secured to tensioning shaft 301 prior to flexible suture 304 being brought proximate to or encircling a bone.

Figure 4:
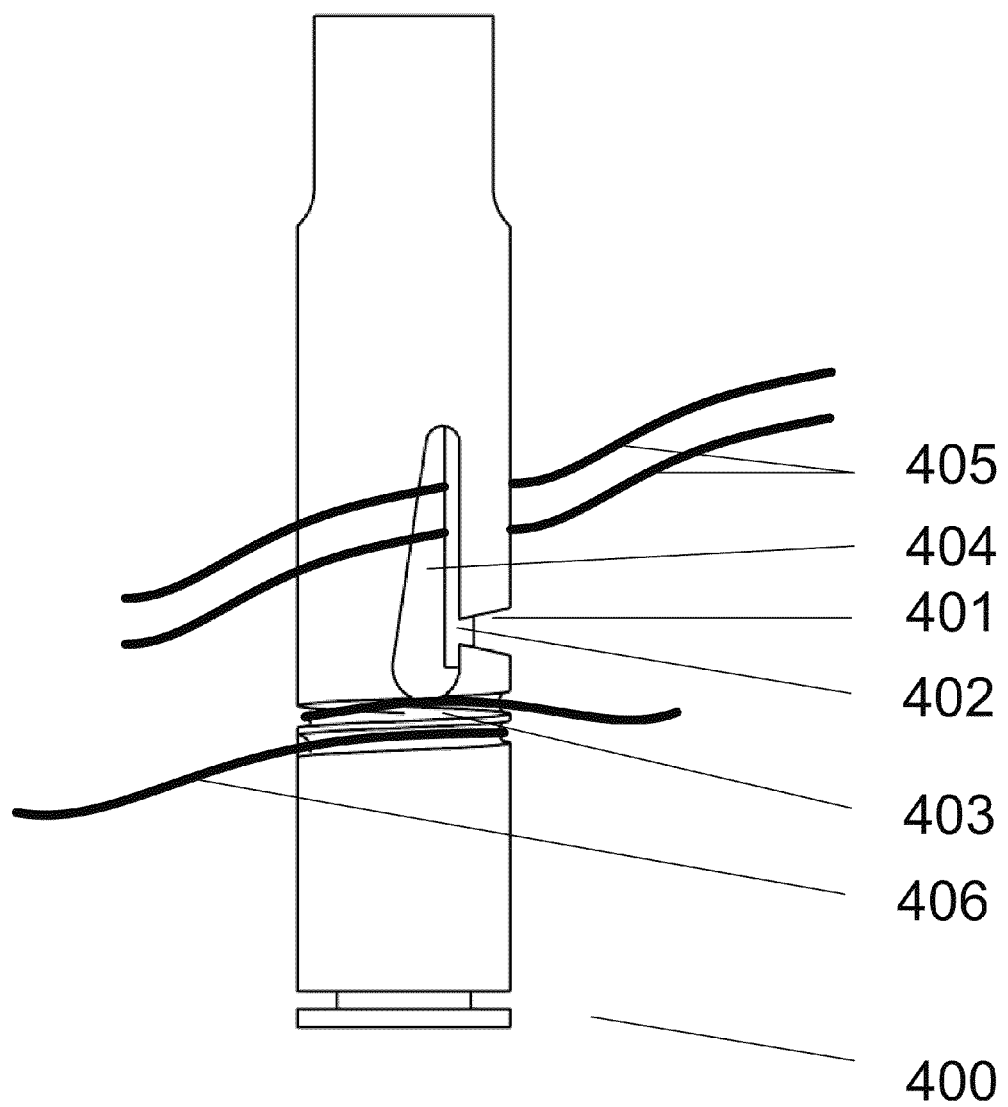
FIG. 4 is a diagram showing a detailed view of a tensioning shaft according to one illustrated embodiment.

FIG. 4 shows an alternate embodiment of a tensioning shaft 400. Opening 401 is large enough that two flexible sutures 405 may easily be pulled into slot 404. One way latch 402 allows flexible sutures 405 to easily enter opening 401 and slot 404, but do not allow flexible sutures 405 to escape from opening 401. Capturing flexible sutures 405 in slot 404 secures flexible sutures 405 to tensioning shaft 400. Another method of securing flexible suture 405 to tensioning shaft 400 is to use groove 403. Flexible suture 406 may be held in groove 403, and rotated together with tensioning shaft 400. As flexible suture 406 is rotated with shaft 400, it becomes secured to tensioning shaft 400. Flexible sutures 405 may be secured to tensioning shaft 400 prior to flexible sutures 405 being brought proximate to or encircling a bone.

Figure 5:
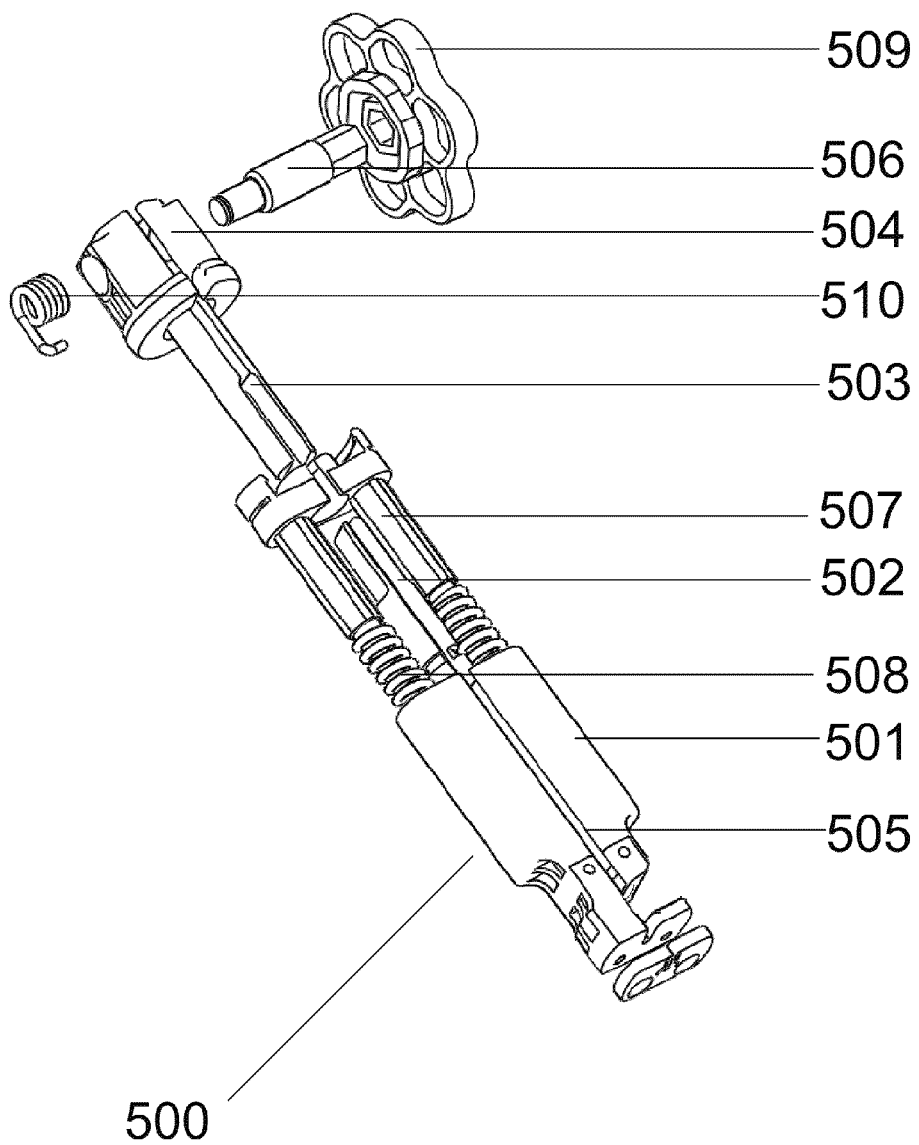
FIG. 5 is a diagram showing an exploded view of a surgical instrument according to one illustrated embodiment.

FIG. 5 shows an exploded view of a surgical instrument 500 according to one illustrated embodiment. Surgical instrument 500 contains base column 501, lower central twisting shaft 502, upper central twisting shaft 503 and twisting head 504. Open slot 505 may be present which runs through the length of surgical instrument 500. Slot 505 allows flexible sutures to be easily loaded into surgical instrument 500 and into tensioning shaft 506. One or more pistons 507 may sit on top of springs 508, which fit into shafts in base column 501. As flexible sutures are twisted around tensioning shaft 506, by rotating tensioning handle 509, tension is applied to the flexible sutures. This tension is maintained by force from springs 508 on pistons 507. As the tension is increased, by further twisting tensioning shaft 506, pistons 507 move downwards into the base column 501 causing springs 508 to compress. The two part design of central twisting shaft 502, 503 enables central twisting shaft 502, 503 to shorten as pistons 507 move downward into base column 501. Lower central twisting shaft 502 is able to move upwards into upper central twisting shaft 503. One way clutch spring 510 fits over tensioning shaft 506 and restricts tensioning shaft 506 to rotate in one direction only. Thus, as tension is applied to the flexible sutures as tensioning shaft 506 is rotated, this tension is maintained, even if tensioning handle 509 is released, as one way clutch spring 510 does not allow tensioning shaft 506 to counter-rotate, which would release the tension. In this way, increasing tension on the flexible sutures may be maintained, until the desired tension is achieved.

Figure 6:
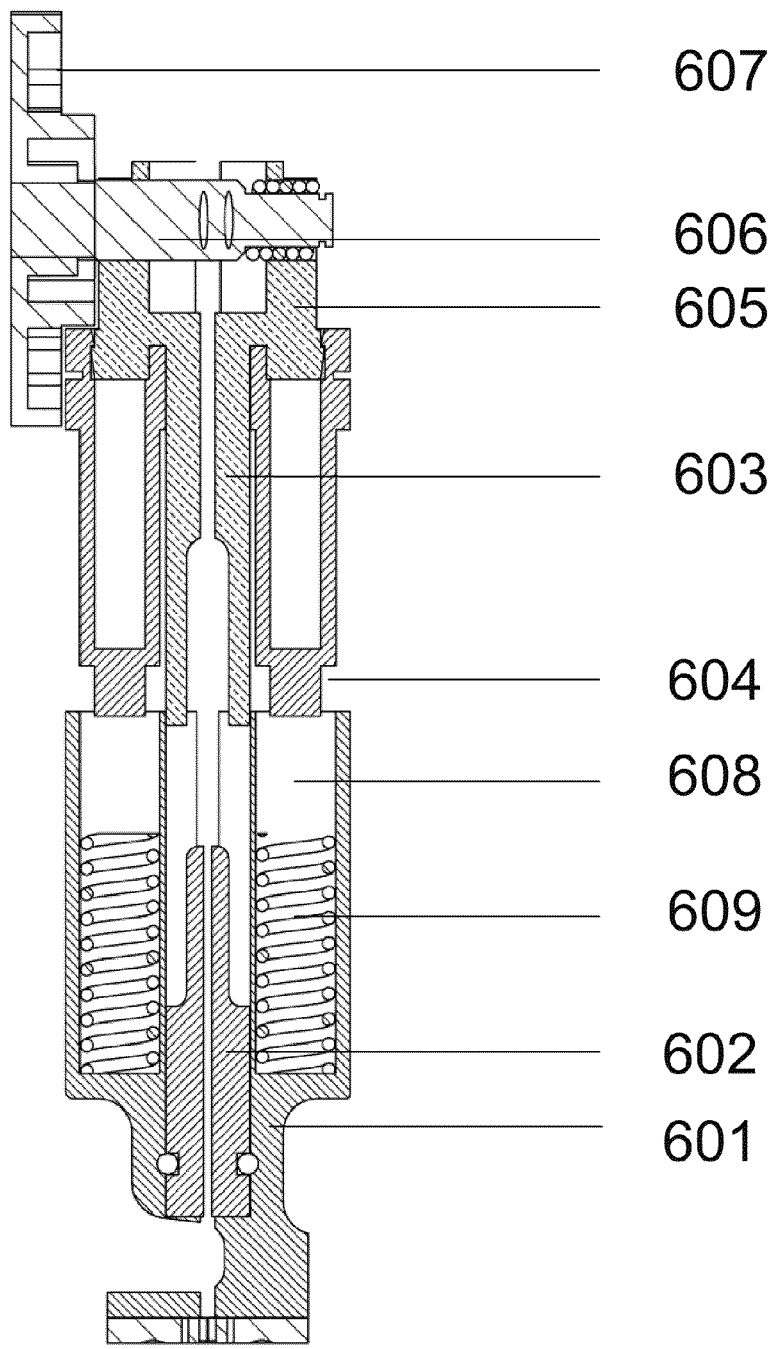
FIG. 6 is a diagram showing a cross sectional view of a surgical instrument according to one illustrated embodiment.

FIG. 6 shows a cross section of one embodiment of a surgical instrument, showing in detail the internal mechanisms. Rotating upper twisting shaft 603 causes lower twisting shaft 602 to rotate. Lower twisting shaft 602 and upper twisting shaft 603 fit together in such a way that they are able to rotate within base column 601, and also may compress together, as pistons 604 move downwards into shafts 608 in base column 601. This mechanism allows twisting head 605, tensioning shaft 606, and tensioning handle 607 also to move downwards. In another embodiment, springs 609 may be replaced by a pneumatic seal at the end of pistons 604. The air trapped in shafts 608 by the pneumatic seal provides resistance to the compression motion of pistons 604 in a similar way to the springs. The surgical instrument may comprise of any number of springs 609, pistons 604, and shafts 608 to provide the desired tension to the flexible suture.

Figure 7:
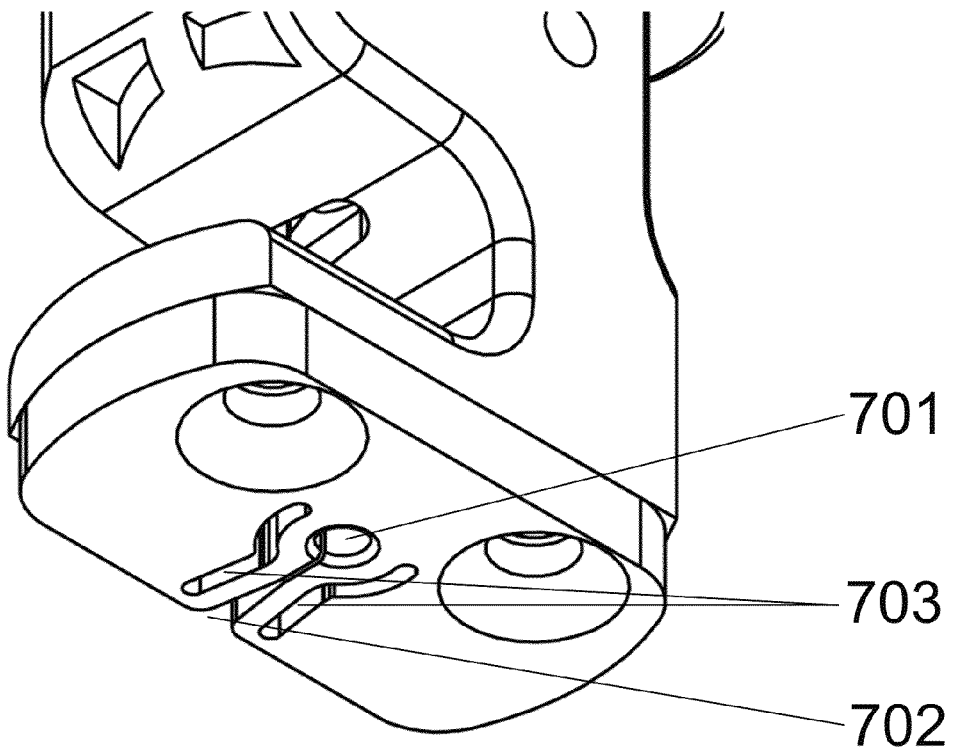
FIG. 7 is a diagram showing a detailed view of a base of a surgical instrument according to one illustrated embodiment.

FIG. 7 shows a base of a surgical instrument in one embodiment, with central opening 701 into which flexible sutures may be drawn through slot 702. The base of the surgical instrument comprises additional flex slots 703, which allow the material surrounding central opening 701 to deform sufficiently to allow the flexible sutures to be drawn easily into central opening 701, where the flexible sutures may be held in place. Once the flexible suture are drawn into central opening 701, the material between central opening 701 and flex slots 703 returns to its relaxed shape and restrains the sutures in central opening 701.

Figure 8:
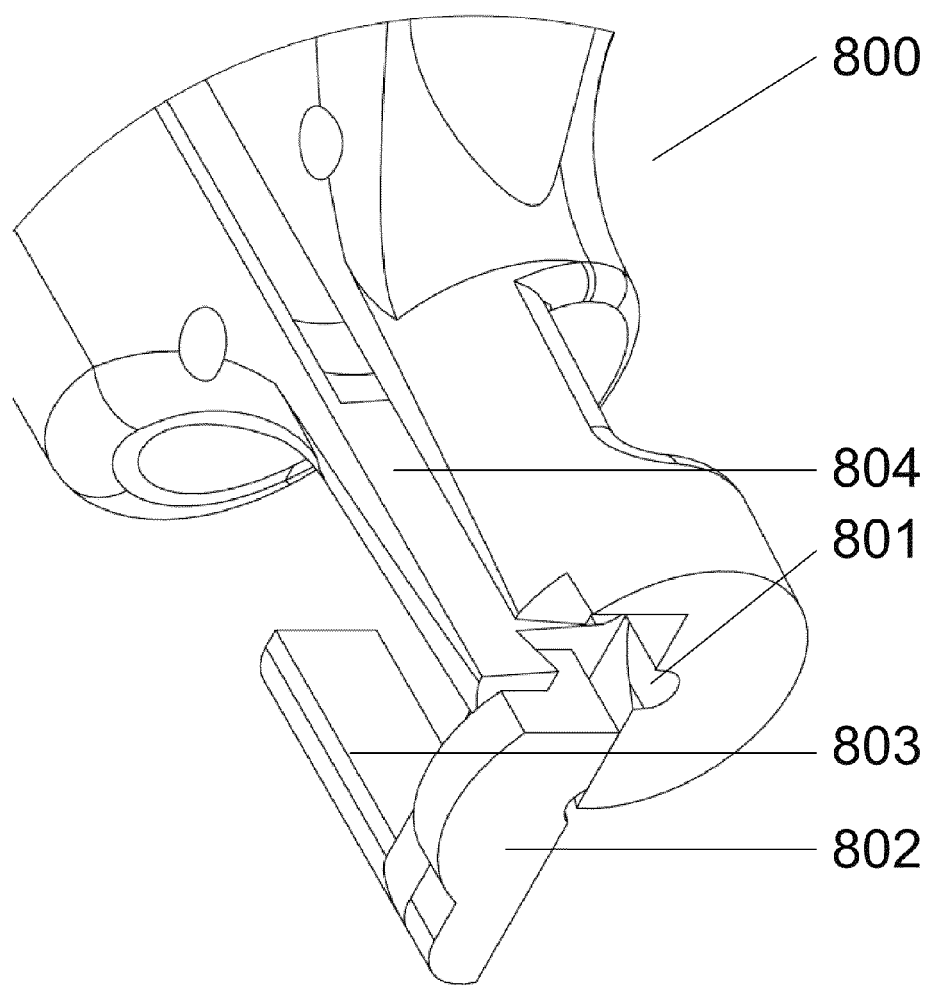
FIG. 8 is a diagram showing a detailed view of a base of a surgical instrument according to another illustrated embodiment.

FIG. 8 shows a base of a surgical instrument 800 in an alternate embodiment, with central opening 801 into which flexible sutures may be drawn. Central opening 801 is initially open, allowing the flexible sutures to easily be drawn into slot 804 which runs vertically through surgical instrument 800. Once the flexible sutures have been drawn into central opening 801, sliding lock 802 may be pushed closed, by pushing on lock handle 803, and so capturing the flexible sutures in central opening 801 in the base of surgical instrument 800.

Figure 9:
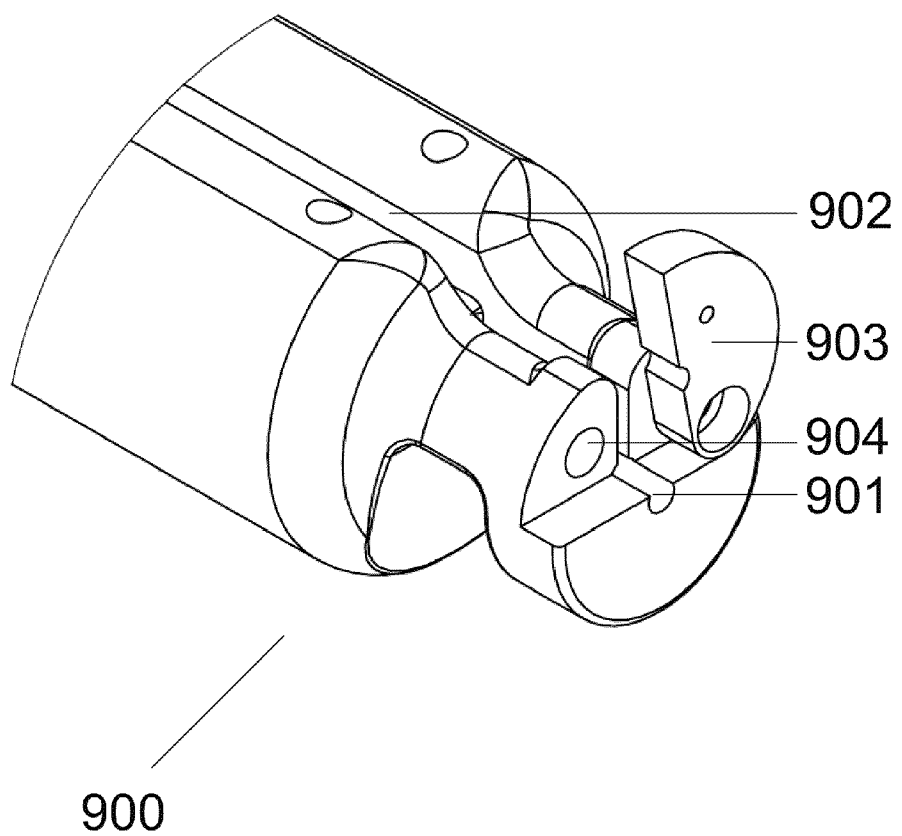
FIG. 9 is a diagram showing a detailed view of a base of a surgical instrument according to another illustrated embodiment.

FIG. 9 shows a base of a surgical instrument in another alternate embodiment, with central opening 901 into which flexible sutures may be drawn. Central opening 901 is initially open, allowing the flexible sutures to easily be drawn into slot 902 which runs vertically through surgical instrument 900. Once the flexible sutures have been drawn into central opening 901, swivel lock 903 may be pushed closed to capture the flexible sutures in central opening 901. Swivel lock 903 may then be held in position by small latch 904 on the base of surgical instrument 900, which locks swivel lock 903 in the closed position.

Figure 10:
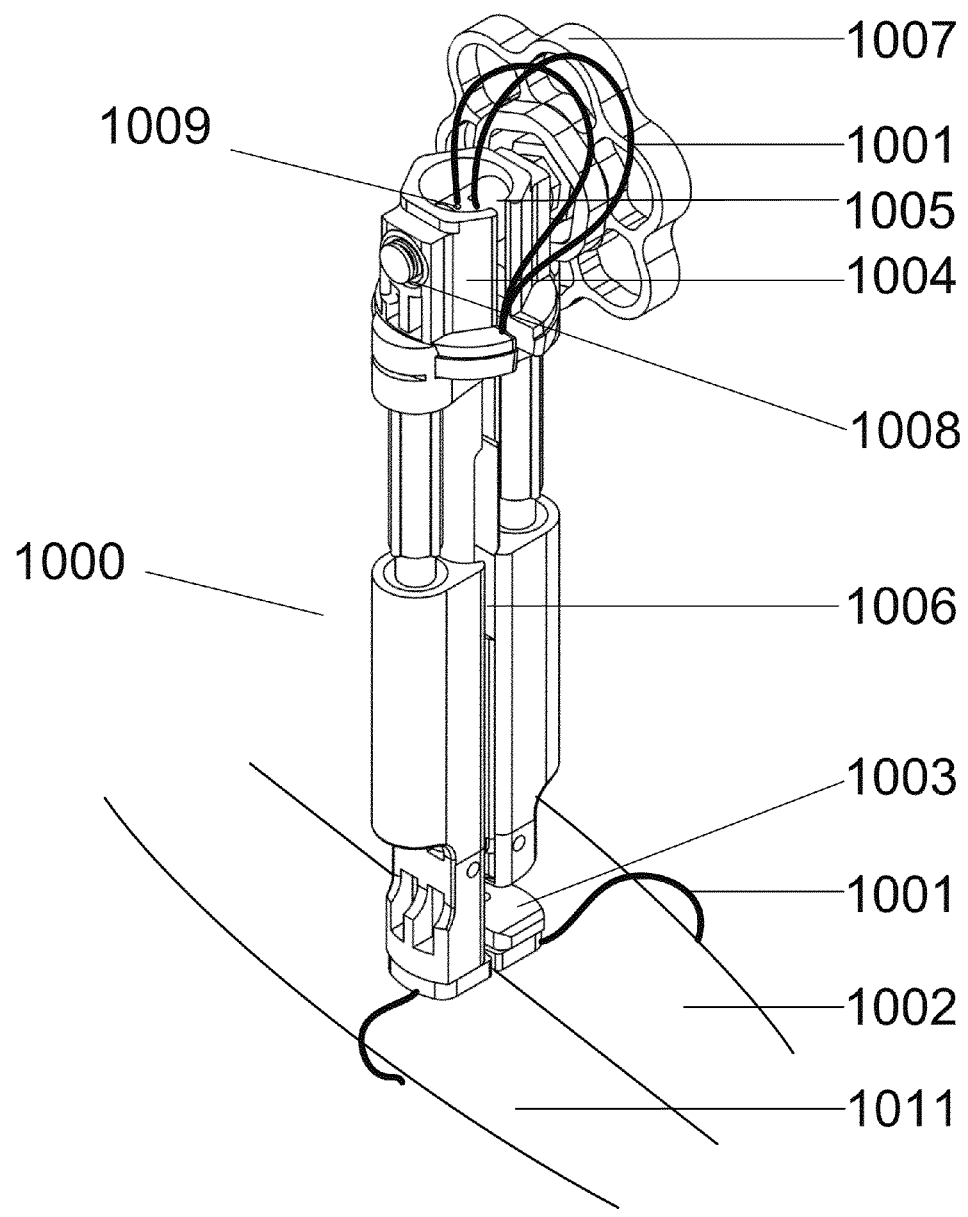
FIG. 10 is a diagram showing a surgical instrument in place on a bone, with flexible sutures, according to one illustrated embodiment.

FIG. 10 is a diagram showing an embodiment of a surgical instrument 1000 being used to tighten flexible sutures around a bone. Flexible suture 1001 is placed around or through parts of bone 1002, 1011 to be secured. The flexible suture 1001 may be drawn through base 1003 of surgical instrument 1000 and upwards through slot opening 1006, towards twisting head 1004 of surgical instrument 1000. Flexible suture 1001 may then be secured in tensioning shaft 1005. Alternatively, flexible suture 1001 may be secured into opening 1009 in tensioning shaft 1005, and then drawn downwards into slot 1006, and then secured in base 1003. Once flexible suture 1001 has been secured in base 1003 and to tensioning shaft 1005, base 1003 may be placed on bone 1002 and tensioning handle 1007 may be rotated to apply tension to flexible suture 1001. Tensioning handle 1007 rotates tensioning shaft 1005, which rotates within one-way clutch mechanism 1008. One-way clutch mechanism 1008 allows tensioning handle 1007 and tensioning shaft 1005 to rotate in only one direction. Rotation of tensioning handle 1007 causes flexible suture 1001 to rotate around tensioning shaft 1005 and applies tension to flexible suture 1001. This tension may be progressively increased by continuing to rotate tensioning handle 1007. Flexible suture 1001 is drawn further up into surgical instrument 1000, through a small opening at the base and tension is applied to the flexible suture 1001 surrounding bone 1002, 1011. As tension is applied, the separated parts of bone 1002, 1011 are drawn together. Tensioning handle 1007 is removable from surgical instrument 1000, which allows multiple surgical instruments to be used together in a restricted space, without tensioning handles 1007 becoming entangled, or impacting the operation of other surgical instruments within close proximity.

Figure 11:
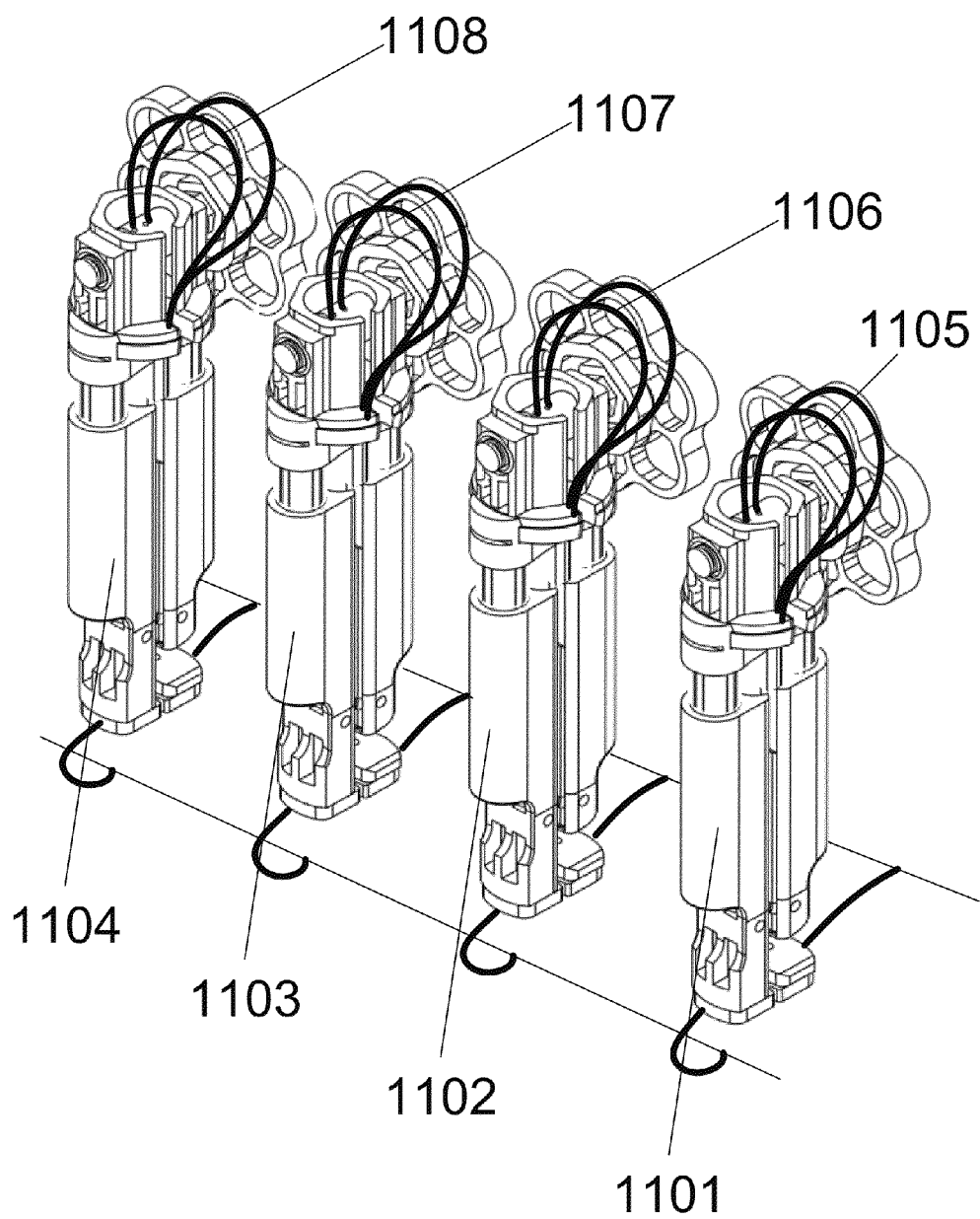
FIG. 11 is a diagram showing multiple surgical instruments in place on a bone, with multiple flexible sutures, according to one illustrated embodiment.

FIG. 11 is a diagram showing an embodiment of multiple surgical instruments being used in parallel to secure a bone. A surgeon may first use surgical instrument 1101 to apply tension to flexible suture 1105. Surgical instrument 1101 may be left in position and second surgical instrument 1102 may now be used to apply tension to second flexible suture 1106. Additional surgical instruments 1103 and 1104 may be added in a similar manner to apply tension to flexible sutures 1107 and 1108. Once two or more surgical instruments have been used to apply tension to two or more different flexible sutures, the surgeon may return to any surgical instrument and increase the tension on the corresponding flexible suture. In this way, multiple surgical instruments may be used in a single procedure to accurately adjust the tension on multiple flexible sutures to the preferred tension. This technique gives the surgeon the ability to precisely adjust each flexible suture to the desired tension required to hold the bone together, and gives the surgeon the ability to increase the tension on any one flexible suture.

Surgical instruments 1101, 1102, 1103, and 1104 may each comprise a mechanism for securing at least one end of flexible sutures 1105, 1106, 1107, 1108 to the surgical instrument prior to the sutures 1105, 1106, 1107, 1108 being brought proximate to or encircling a bone.

Figure 12:
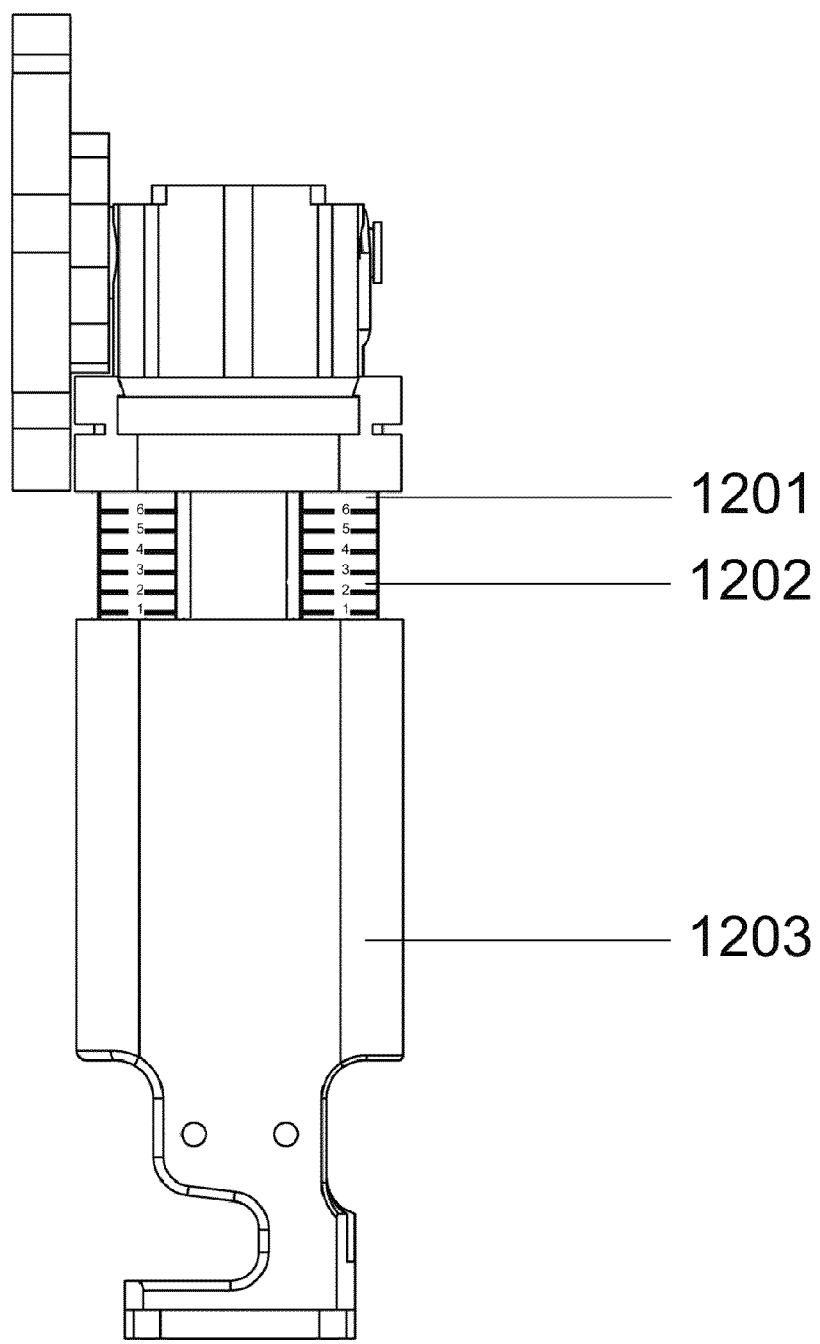
FIG. 12 is a diagram showing a detailed view of a piston assembly with a tension indicator, according to one illustrated embodiment

FIG. 12 shows a detailed view of one embodiment of a piston assembly and tension indicator. Piston 1201 may include tension indicator 1202, which gives the surgeon an indication of the tension that is being applied to the flexible suture. As more tension is applied to the flexible suture, piston 1201 may move downward into the shaft in base column 1203. This movement may be used to give an indication on piston 1201 of the distance that piston 1201 has moved, and also of the tension that has been applied to the flexible suture.

Once the surgeon is satisfied that all flexible sutures are the desired tension and that the bone is securely held by all the flexible sutures used in the procedure, the surgeon may then begin to secure the flexible sutures in place by twisting each flexible suture together on itself.

Figure 13:
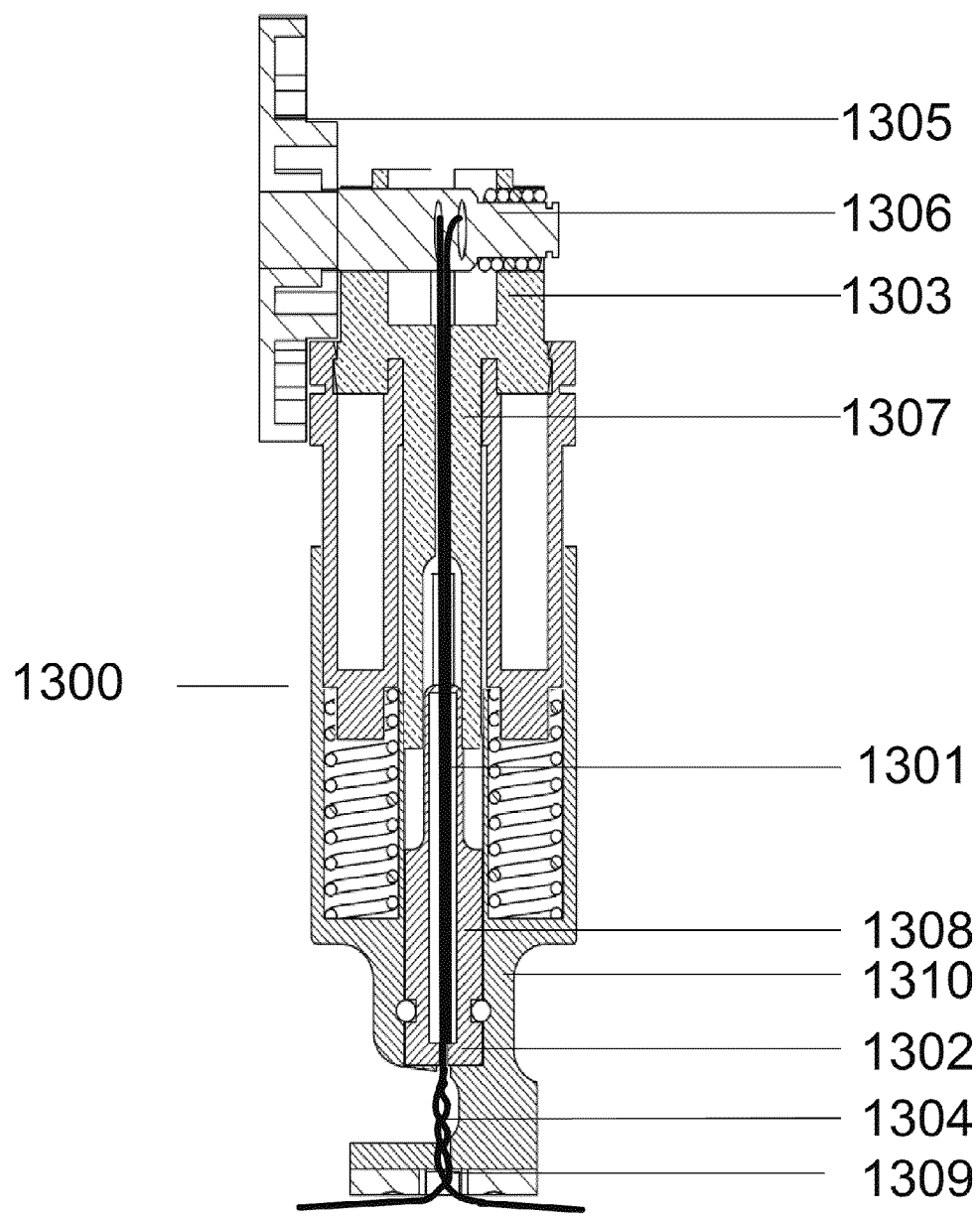
FIG. 13 is a diagram showing a side view of a surgical instrument with flexible sutures, according to one illustrated embodiment

FIG. 13 shows an embodiment of a surgical instrument 1300 that is able to apply a twist to a flexible suture after the suture has been appropriately tensioned. Twisting head 1303 may be twisted in either a clockwise or anticlockwise direction around the central axis of base column 1310. The entire head assembly including tensioning handle 1305, tensioning shaft 1306 and twisting head 1303 rotate in the direction of rotation applied to twisting head 1303. Base column 1310 does not rotate. This twisting motion of twisting head 1303 is translated into a twisting motion of both upper central twisting shaft 1307 and lower central twisting shaft 1308. Lower central twisting shaft 1308 comprises narrow portion 1302 which restricts the two ends of flexible suture 1301 from twisting about each other within the narrow portion 1302. As lower central twisting shaft 1308 is rotated, the two ends of flexible suture 1301 below narrow portion 1302 begin to twist around each other. This action forms twisted part 1304 of flexible suture 1301 between narrow portion 1302 of lower central twisting shaft 1308 and the narrow opening in the base 1309 of the surgical instrument. After a preferred number of complete rotations of twisting head 1303, flexible suture 1301 may now be sufficiently twisted to provide a secure locking mechanism for flexible suture 1301 that has been applied to the bone. The surgeon may repeat this twisting procedure on each of the surgical instruments that may have been used to secure and tension the flexible sutures on the patient's bone.

Figure 14:
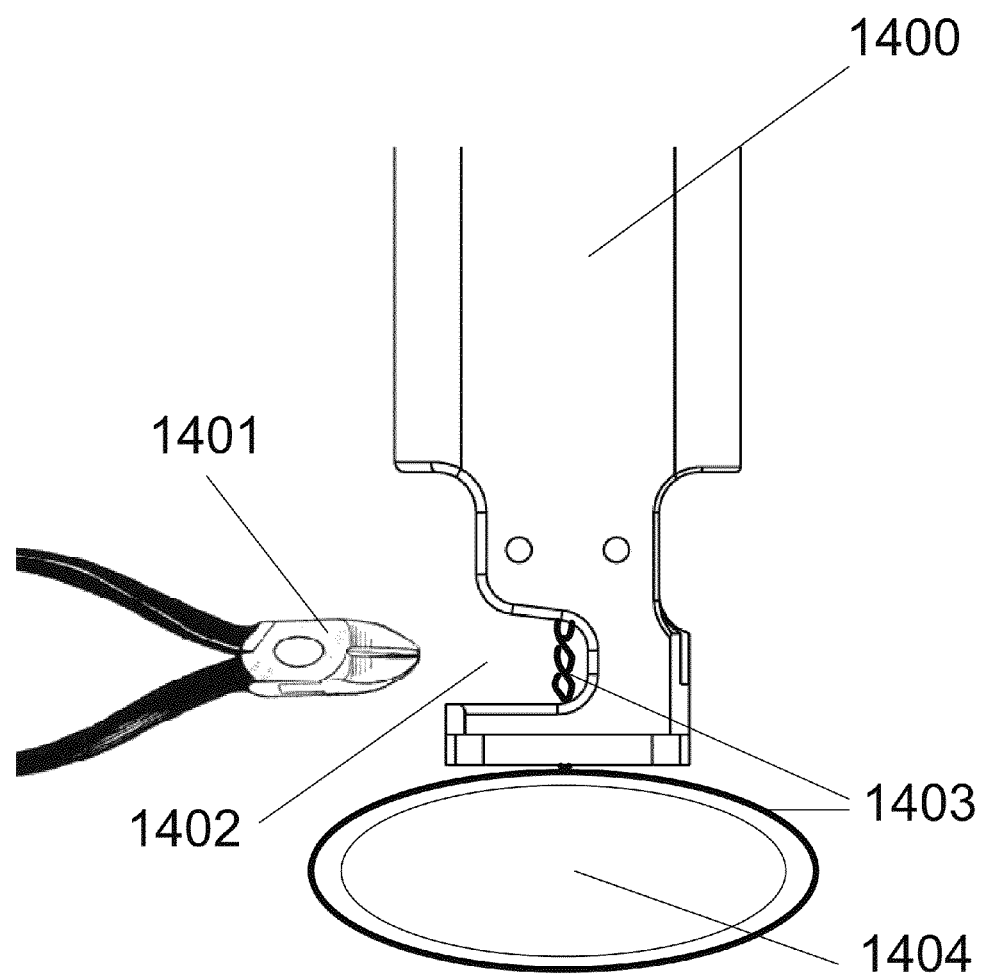
FIG. 14 is a diagram showing cutters being used to cut flexible sutures held within a surgical instrument according to one illustrated embodiment.

FIG. 14 is a diagram showing an embodiment of how a flexible suture may be cut after being tensioned and twisted. Surgical cutters 1401 may be inserted into cutter opening 1402 and cut the twisted flexible suture. Alternatively, surgical instrument 1400 may include a blade for automatically cutting flexible suture 1403. Cutting flexible suture 1403 will release surgical instrument 1400 from flexible suture 1403 attached to bone 1404 and allow surgical instrument 1400 to be removed. In another embodiment of surgical instrument 1400, the narrow part of the lower central twisting shaft (not shown) will be sufficiently narrow or comprise an edge to weaken the flexible sutures that pass through surgical instrument 1400. When a sufficient number of twists have been applied to flexible suture 1403, flexible suture 1403 will automatically break at the top of the twisted section, and release surgical instrument 1400 from the twisted flexible suture 1403.

Figure 15:
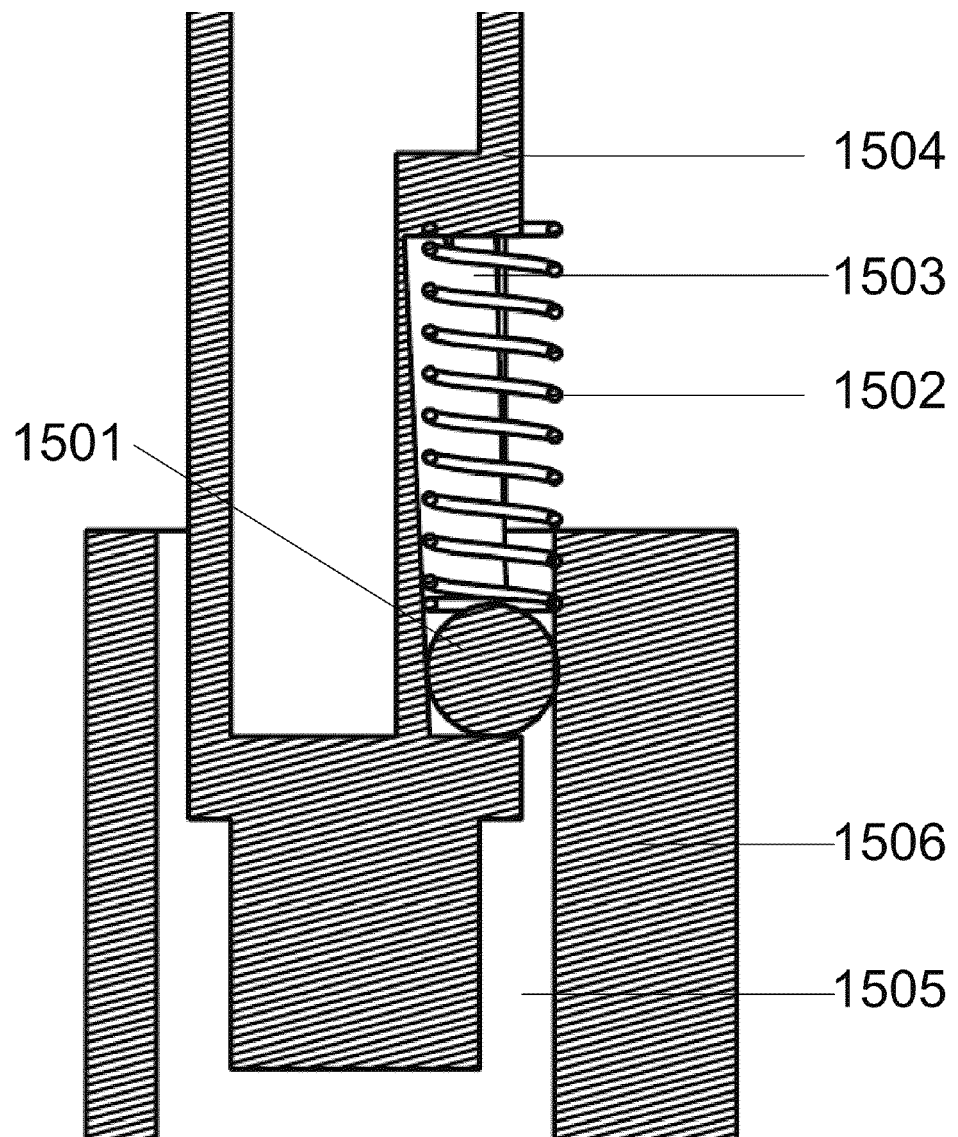
FIG. 15 is a diagram showing a detailed view of a piston assembly, according to one illustrated embodiment.

FIG. 15 shows a detailed view of an embodiment of a one way mechanism on the piston assembly. Piston 1504 may include a mechanism for preventing the head assembly of a surgical instrument from jumping up after cutting a flexible suture loaded into the surgical instrument. Ball 1501 is held in place by spring 1502 in cavity 1503 within piston 1504. When piston 1504 is pushed into shaft 1505 in base column 1506, spring 1502 is compressed, ball 1501 moves into cavity 1503, and piston 1504 is able to move downwards. Piston 1504 is restricted from moving upward and out of shaft 1505 as any upward motion causes ball 1502 to be forced against the wall of shaft 1505 causing sufficient friction such that piston 1504 is unable to move upwards.

Figure 16:
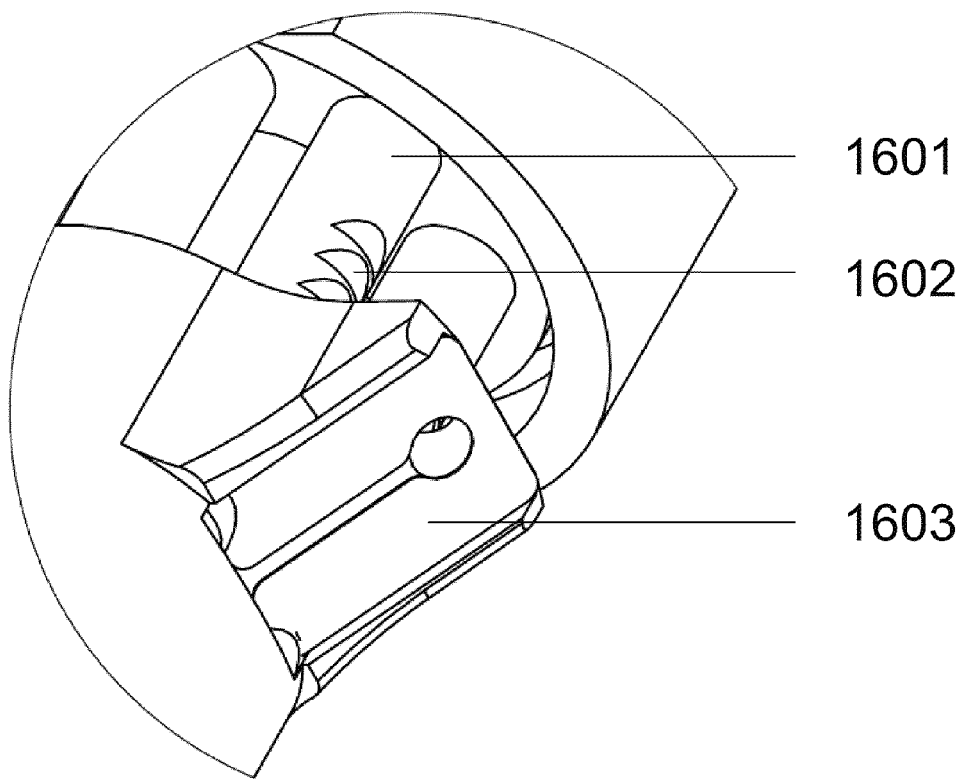
FIG. 16 is a diagram showing a detailed view of a piston assembly, according to another illustrated embodiment.

FIG. 16 shows a detailed view of an embodiment of a one way mechanism on the piston assembly for preventing the head assembly of a surgical instrument from jumping up, after cutting a flexible suture loaded into the surgical instrument. Piston 1601 may have slots 1602 cut into it at regular intervals. Flexible blade 1603 is held with one edge lying at an angle within slots 1602, allowing piston 1601 to move downwards. As piston 1601 moves downwards, blade 1603 may move from one slot 1602 to the one above it. Blade 1603 is able to move easily from one slot to the one above due to the angular orientation of blade 1603 within slot 1602. If piston 1601 attempts to move upwards, the angle of blade 1603 within slot 1602 resists this movement and prevents piston 1601 from moving upwards.

Figure 17:
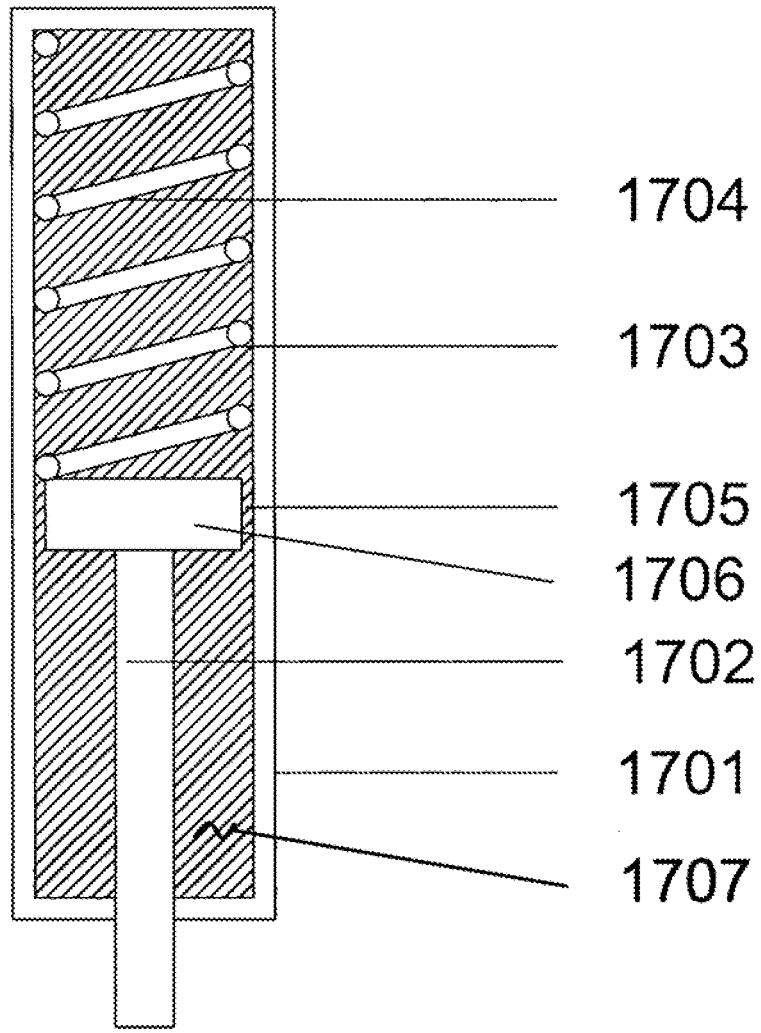
FIG. 17 is a diagram showing a cross sectional view of a piston assembly, according to another illustrated embodiment.

FIG. 17 shows a detailed view of an embodiment of a one way mechanism on the piston assembly for preventing the head assembly of a surgical instrument from jumping up, after cutting a flexible suture loaded into the surgical instrument. In a cross sectional view of shaft 1701 in the base column, spring 1703 inside shaft 1701 in the base column may be enclosed in fluid 1704. Piston 1702 fits into shaft 1701 in the base column, with gap 1705 around piston head 1706. As piston 1702 moves downwards into openings 1707 in the base column, spring 1703 slowly compresses, and fluid 1704 is able to move through gap 1705 around piston head 1706. When tension is released by cutting the flexible suture, piston 1702 moves upwards under pressure from spring 1703. This movement is restricted by the flow of fluid 1704 around piston head 1706. This provides a slow upward movement of piston 1702, preventing the head assembly of the surgical instrument mechanism from jumping up.

What is claimed is:

1. A surgical instrument comprising:
a base comprising a bone contacting surface that in use contacts at least a portion of at least one bone,
a first device movably coupled with respect to the base and including a handle rotatable about a first axis, the first device operable in response to at least a partial rotation of the handle to tension a flexible suture extending about at least the portion of the at least one bone and concurrently reduce a distance between the handle and the bone contacting surface; and
a second device including at least one portion rotatable with respect to the base about a second axis, the second device operable in response to rotation of the at least one portion thereof about the second axis to apply a plurality of twists to the flexible suture while the tension in the flexible suture is maintained.

2. The surgical instrument of claim 1 wherein said flexible suture is a stainless steel wire suture.

3. The surgical instrument of claim 1 wherein said base comprises an open slot sized to receive a portion of the flexible suture and the surgical instrument further comprises at least one member movable to selectively constrain the flexible suture in the slot.

4. The surgical instrument of claim 1 wherein the second axis is not parallel to the first axis.

5. The surgical instrument of claim 1 wherein the surgical instrument further comprises a sized slot to accommodate a portion of a tool to allow cutting of the flexible suture by the tool.

6. The surgical instrument of claim 1 wherein the surgical instrument further comprises a third device comprising an edge that breaks the flexible suture when a sufficient number of the plurality of twists have been applied to the flexible suture.

7. The surgical instrument of claim 1 wherein the first device comprises a tensioning shaft and a one way clutch, the tensioning shaft rotatably mounted with respect to a portion of the surgical instrument and comprising a flexible suture retaining structure to retain the flexible suture, and the one way clutch operably coupled to the tensioning shaft to limit rotation of the tensioning shaft to a single rotational direction.

8. The surgical instrument of claim 1, further comprising:
a spring arranged to maintain the tension in the flexible suture at least in part when the second device applies the plurality of twists to the flexible structure.

9. The surgical instrument of claim 1 wherein the second device applies the plurality of twists to the flexible suture to secure the flexible suture extending about the portion of the at least one bone.

10. The surgical instrument of claim 1 wherein the second device applies the plurality of twists to the flexible suture to secure portions of the flexible suture together.

11. The surgical instrument of claim 1 wherein the second device comprises a twisting head in which one or more portions of the flexible suture are retained, the twisting head rotatably mounted to the base to rotate with respect thereto and apply the plurality of twists to the flexible suture while the tension in the flexible suture is maintained.

12. The surgical instrument of claim 1 wherein the second device comprises a twisting head in which one or more portions of the flexible suture are retained, the twisting head rotatable with respect to the bone contacting surface about the second axis to apply the plurality of twists to the flexible suture while the tension in the flexible suture is maintained, and the first device comprises a tensioning shaft including a flexible suture retaining structure to retain the flexible suture, the tensioning shaft rotatable about the first axis to tension the flexible suture.

13. The surgical instrument of claim 12 wherein the tensioning shaft is coupled to the twisting head such that a rotation of the twisting head about the second axis rotates the tensioning shaft about the second axis when the second device applies the plurality of twists to the flexible suture while the tension in the flexible suture is maintained.

14. The surgical instrument of claim 1 wherein the first device comprises a tensioning shaft comprising a flexible suture retaining structure to retain the flexible suture, the tensioning shaft arranged to rotate about a tensioning shaft rotation axis to tension the flexible suture, the tensioning shaft movably coupled to the base to vary a distance between the tensioning shaft and the bone contacting surface of the base when tensioning the flexible suture.

15. The surgical instrument of claim 14 wherein the handle is physically coupled to the tensioning shaft and the surgical instrument comprises a one-way clutch physically coupled to the tensioning shaft to restrict rotation of the tensioning shaft about the tensioning shaft rotation axis to a single rotational direction.

16. The surgical instrument of claim 14 further comprising a spring positioned between the tensioning shaft and the base arranged to apply a varying spring force to the flexible suture as the tensioning shaft is rotated about the tensioning shaft rotation axis to vary the distance between the tensioning shaft and the bone contacting surface of the base.

17. The surgical instrument of claim 1 wherein the second device comprises a twisting head in which one or more portions of the flexible suture are retained, the twisting head rotatably mounted to the base for rotation with respect thereto about a twisting head rotation axis to apply the plurality of twists to the flexible suture while the tension in the flexible suture is maintained, the twisting head further movably coupled to the base to vary a distance between the twisting head and the bone contacting surface of the base when the twisting head is rotated about the twisting head rotational axis.

18. The surgical instrument of claim 17 wherein the twisting head moves along a direction parallel to the twisting head rotation axis when the twisting head is rotated about the twisting head rotation axis.

19. The surgical instrument of claim 17 wherein the second device further comprises at least a first twisting member and at least a second twisting member, each of at least the first and the second twisting members positioned between the twisting head and the base, the first twisting member rotationally coupled to the second twisting member to transfer torque between the first twisting member and the second twisting member when the twisting head is rotated about the twisting head rotation axis, and the first twisting member further physically coupled to the second twisting member to allow relative translational movement therebetween when the twisting head is rotated about the twisting head rotation axis.

20. The surgical instrument of claim 1, further comprising a slot that extends through the base and at least a portion of the at least one portion of the second device that is rotatable with respect to the base about the second axis.

21. A surgical instrument to secure a flexible suture to at least one body part, the surgical instrument comprising:
a base;
a twisting head rotatably mounted to the base to rotate with respect thereto about a first axis to secure portions of the flexible suture together;
a tensioning shaft comprising a flexible suture retaining structure, the tensioning shaft rotatably mounted to the twisting head to rotate with respect thereto about a second axis to apply tension to the flexible suture; and
a handle physically coupled to the tensioning shaft, the handle operable to rotate the tensioning shaft about the second axis,
wherein the twisting head is movably coupled to the base for movement with respect thereto along a direction parallel to the first axis to reduce a distance between the twisting head and a surface of the base when the tensioning shaft is rotated about the second axis to apply tension to the flexible suture.

22. The surgical instrument of claim 21, further comprising: a one way clutch, the one way clutch physically coupled between the handle and the twisting head and arranged to limit rotation of the handle to a single rotational direction.

23. The surgical instrument of claim 22 wherein the one way clutch comprises a spring.

24. The surgical instrument of claim 21 wherein the twisting head is rotatable about the first axis to apply a plurality of twists to the flexible suture to secure the portions of the flexible suture together.

25. The surgical instrument of claim 21 wherein the twisting head is rotatable about the first axis to apply at least one twist to the flexible suture to secure the flexible suture encircled about a portion of the at least one body part.

26. The surgical system of claim 21 wherein the surface of the base is positioned on the base to contact with the at least one body part when the tensioning shaft is rotated about the second axis to apply tension to the flexible suture.

27. The surgical system of claim 26 wherein the surface of the base is positioned on the base to contact with the at least one body part when the twisting head is rotated about the first axis to secure portions of the flexible suture together.

28. The surgical system of claim 21, further comprising a spring physically coupled between the twisting head and the base, the spring arranged to apply a spring force to the flexible suture that varies as the distance between the twisting head and the surface of the base is varied.

29. The surgical instrument of claim 21 wherein the twisting head is movably coupled to the base for movement with respect thereto along a direction parallel to the first axis to vary a distance between the twisting head and the surface of the base when the twisting head is rotated about the first axis.

30. The surgical instrument of claim 29, further comprising a spring physically coupled between the twisting head and the base, the spring arranged to apply a spring force to the flexible suture that varies as the distance between the twisting head and the surface of the base is varied.

31. The surgical instrument of claim 21, further comprising a spring arranged to apply a spring force to the flexible suture, a dimension of the spring varying during at least one of a rotation of the twisting head about the first axis and a rotation of the tensioning shaft about the second axis.

32. The surgical instrument of claim 21 wherein the second axis is non-parallel to the first axis.

33. The surgical instrument of claim 21, further comprising a slot that extends through the base and at least a portion of the twisting head.

34. A surgical instrument, comprising:
a first device comprising a handle selectively operable to apply tension to a flexible suture extending around about a portion of at least one bone;
a second device selectively operable to apply a number of twists to the flexible suture; and
a base comprising a bone contacting surface to contact the at least one bone when the second device applies the number of twists to the flexible suture, wherein the second device is moveably coupled to the base to rotate with respect thereto to apply the number of twists to the flexible suture and to reduce a distance between the second device and the bone contacting surface of the base when the second device applies the number of twists to the flexible suture.

35. The surgical instrument of claim 34 wherein at least the first device maintains the tension in the flexible suture when the second device applies the number of twists to the flexible suture.

36. The surgical instrument of claim 35 wherein the first device comprises a tensioning shaft comprising a flexible suture retaining structure to retain the flexible suture, the tensioning shaft rotatably mounted in the surgical instrument, and the first device further comprising a one way clutch operably coupled to the tensioning shaft to limit rotation of the tensioning shaft to a single rotational direction.

37. The surgical instrument of claim 36, further comprising a spring arranged to maintain the tension in the flexible suture at least in part when the second device applies the number of twists to the flexible structure.

38. The surgical instrument of claim 34 wherein the number of twists secure the flexible suture in an encircled configuration about the portion of the at least one bone.

39. The surgical instrument of claim 34 wherein the second device comprises a twisting head in which one or more portions of the flexible suture are retained, the twisting head rotatable with respect to the base about a first axis to apply the number of twists to the flexible suture, and the first device comprises a tensioning shaft including a flexible suture retaining structure to retain the flexible suture, the tensioning shaft arranged to rotate about a second axis to tension the flexible suture, the second axis non-parallel to the first axis.

40. The surgical instrument of claim 34 wherein the first device comprises a tensioning shaft comprising a flexible suture retaining structure to retain the flexible suture, the tensioning shaft arranged to rotate about a rotation axis to tension the flexible suture, the tensioning shaft movably coupled to the base to vary a distance between the tensioning shaft and the bone contacting surface of the base when tensioning the flexible suture.

41. The surgical instrument of claim 40 wherein the handle is physically coupled to the tensioning shaft and the surgical instrument comprises a one-way clutch physically coupled to the tensioning shaft to restrict rotation of the tensioning shaft about the rotation axis to a single rotational direction.

42. The surgical instrument of claim 41, further comprising a spring positioned between the tensioning shaft and the base, the spring arranged to apply a varying spring force to the flexible suture as the tensioning shaft is rotated about the rotation axis to vary the distance between the tensioning shaft and the bone contacting surface of the base.

43. The surgical instrument of claim 34 wherein the second device comprises a twisting head in which one or more portions of the flexible suture are retained, the twisting head rotatably mounted to the base for rotation with respect thereto about a rotation axis to apply the number of twists to the flexible suture, the twisting head further movably coupled to the base to move along a direction parallel to the rotation axis when the twisting head is rotated about the rotation axis.

44. The surgical instrument of claim 34, further comprising a slot that extends through the base and at least a portion of the second device.

45. The surgical instrument of claim 34 wherein the first device is selectively operable to apply the tension to the flexible suture while concurrently reducing a distance between at least a portion of the first device and the bone contacting surface.

* * * * *